United States Patent
Batchelor et al.

(10) Patent No.: US 11,925,421 B2
(45) Date of Patent: Mar. 12, 2024

(54) ANTI-PERFORATION DEVICE

(71) Applicant: GYRUS ACMI, INC., Southborough, MA (US)

(72) Inventors: Kester J. Batchelor, Mound, MN (US); Nikhil M. Murdeshwar, Maple Grove, MN (US)

(73) Assignee: Gyrus ACMI, Inc., Westborough, MA (US)

(*) Notice: Subject to any disclaimer, the term of this patent is extended or adjusted under 35 U.S.C. 154(b) by 0 days.

(21) Appl. No.: 17/857,791

(22) Filed: Jul. 5, 2022

(65) Prior Publication Data
US 2022/0401159 A1     Dec. 22, 2022

Related U.S. Application Data

(63) Continuation of application No. 16/369,442, filed on Mar. 29, 2019, now Pat. No. 11,406,454.

(51) Int. Cl.
| A61B 5/05 | (2021.01) |
| A61B 34/20 | (2016.01) |
| A61B 90/00 | (2016.01) |
| A61M 25/06 | (2006.01) |

(52) U.S. Cl.
CPC .............. *A61B 34/20* (2016.02); *A61B 90/03* (2016.02); *A61M 25/065* (2013.01); *A61B 2034/2063* (2016.02); *A61B 90/06* (2016.02); *A61M 2025/0687* (2013.01)

(58) Field of Classification Search
CPC ............. A61B 34/20; A61B 2034/263; A61M 25/065; A61M 2025/0687
See application file for complete search history.

(56) References Cited

U.S. PATENT DOCUMENTS

| 4,546,773 A | 10/1985 | Kremer et al. |
| 4,674,503 A | 6/1987 | Peyman et al. |
| 5,486,188 A | 1/1996 | Smith |
| 5,772,597 A | 6/1998 | Goldberger et al. |

(Continued)

FOREIGN PATENT DOCUMENTS

| CN | 111743637 A | 10/2020 |
| EP | 2478856 A1 | 7/2012 |

(Continued)

OTHER PUBLICATIONS

"U.S. Appl. No. 16/369,442, Non Final Office Action dated Jul. 22, 2021", 12 pgs.

(Continued)

*Primary Examiner* — Joel F Brutus
(74) *Attorney, Agent, or Firm* — Schwegman Lundberg & Woessner, P.A.

(57) ABSTRACT

A surgical needle comprising: (a) a sensor; (b) a distal tip with the sensor being located at the distal tip; (c) a needle advancing mechanism that is adjustable to change an insertion depth; and (d) a control unit in communication with the needle advancing mechanism; wherein the sensor provides a signal to the control unit regarding a thickness of a feature of interest and the control unit controls the insertion depth based upon the signal from the sensor so that the insertion depth into the feature of interest is varied or the control unit prevents the needle advancing mechanism from activating.

18 Claims, 5 Drawing Sheets

(56) References Cited

U.S. PATENT DOCUMENTS

| | | |
|---|---|---|
| 8,510,012 B2 | 8/2013 | Amato et al. |
| 8,670,816 B2 | 3/2014 | Green et al. |
| 8,939,111 B2 | 1/2015 | Berntsen |
| 9,320,539 B2 | 4/2016 | Daniel et al. |
| 9,332,990 B2 | 5/2016 | Requarth |
| 9,757,535 B2 | 9/2017 | Rajagopalan et al. |
| 9,844,641 B2 | 12/2017 | Rajagopalan et al. |
| 11,406,454 B2 | 8/2022 | Batchelor et al. |
| 2003/0028172 A1 | 2/2003 | Epstein et al. |
| 2004/0236358 A1 | 11/2004 | Barrile-josephson et al. |
| 2007/0135803 A1 | 6/2007 | Belson |
| 2008/0097501 A1 | 4/2008 | Blier |
| 2010/0058603 A1 | 3/2010 | Hoffman |
| 2010/0094116 A1 | 4/2010 | Silverstein |
| 2012/0101370 A1 | 4/2012 | Razzaque et al. |
| 2012/0326875 A1 | 12/2012 | Coppola |
| 2014/0142422 A1* | 5/2014 | Manzke .............. A61B 8/12 600/424 |
| 2014/0309522 A1 | 10/2014 | Fullerton et al. |
| 2015/0008248 A1 | 1/2015 | Giordano et al. |
| 2015/0157787 A1 | 6/2015 | Cully et al. |
| 2015/0201944 A1 | 7/2015 | Starnes |
| 2015/0238276 A1 | 8/2015 | Atarot et al. |
| 2016/0106554 A1 | 4/2016 | Lavallee |
| 2016/0166351 A1 | 6/2016 | Kleiner |
| 2016/0338679 A1* | 11/2016 | Tehrani .............. A61B 5/061 |
| 2017/0252060 A1 | 9/2017 | Ellingson et al. |
| 2018/0193590 A1 | 7/2018 | Rajagopalan et al. |
| 2020/0305981 A1 | 10/2020 | Batchelor et al. |

FOREIGN PATENT DOCUMENTS

| | | |
|---|---|---|
| EP | 2997926 A1 | 3/2016 |
| EP | 3162294 A1 | 5/2017 |
| ES | 2216124 T3 | 10/2004 |
| JP | H05337127 | 12/1993 |
| JP | 2005509488 | 4/2005 |
| JP | 2012531276 | 12/2012 |
| WO | WO-9835720 A2 | 8/1998 |
| WO | WO-9927839 A2 | 6/1999 |
| WO | WO-0108578 A1 | 2/2001 |
| WO | WO-03011394 A1 | 2/2003 |
| WO | 03043536 | 5/2003 |
| WO | WO-2011021192 A1 | 2/2011 |
| WO | WO-2014066042 A2 | 5/2014 |
| WO | WO-2015138708 A1 | 9/2015 |
| WO | 2016160348 | 10/2016 |

OTHER PUBLICATIONS

"U.S. Appl. No. 16/369,442, Non Final Office Action dated Dec. 8, 2021", 12 pgs.

"U.S. Appl. No. 16/369,442, Notice of Allowance dated Mar. 30, 2022", 8 pgs.

"U.S. Appl. No. 16/369,442, Response filed Mar. 8, 2022 to Non Final Office Action dated Dec. 8, 2021", 13 pgs.

"U.S. Appl. No. 16/369,442, Response filed Oct. 21, 2021 to Non Final Office Action dated Jul. 22, 2021", 14 pgs.

"European Application Serial No. 20166758.1, Communication Pursuant to Article 94(3) EPC dated May 6, 2022", 7 pgs.

"European Application Serial No. 20166758.1, Communication Pursuant to Article 94(3) EPC dated Jul. 21, 2021", 7 pgs.

"European Application Serial No. 20166758.1, Extended European Search Report dated Jul. 21, 2020", 10 pgs.

"European Application Serial No. 20166758.1, Response filed Mar. 26, 2021 to Extended European Search Report dated Jul. 21, 2020", 10 pgs.

"European Application Serial No. 20166758.1, Response filed Sep. 7, 2022 to Communication Pursuant to Article 94(3) EPC dated May 6, 2022", 13 pgs.

"European Application Serial No. 20166758.1, Response Filed Nov. 22, 2021 to Communication Pursuant to Article 94(3) EPC dated Jul. 21, 2021", 11 pgs.

Ezedinma, N. Adaobi, et al., "Transvaginal Hydrolaparoscopy", JSLS, (2012), 461-465.

U.S. Appl. No. 16/369,442, U.S. Pat. No. 11,406,454, filed Mar. 29, 2019, Anti-Perforation Device.

"European Application Serial No. 20166758.1, Communication Pursuant to Article 94(3) EPC dated Feb. 7, 2023", 7 pgs.

"Japanese Application Serial No. 2020-58276, Notification of Reasons for Rejection dated Oct. 2, 2023", W English Translation, 19 pgs.

"Chinese Application Serial No. 202010230057.6, Notice of Reexamination dated Oct. 7, 2023", w English Translation, 22 pgs.

\* cited by examiner

ANTI-PERFORATION DEVICE

CROSS-REFERENCE TO RELATED APPLICATIONS

This application is a continuation of U.S. patent application Ser. No. 16/369,442, filed Mar. 29, 2019, which is incorporated by reference herein in its entirety.

FIELD

The present teachings relate to a surgical device with a control unit for controlling a depth of penetration of the surgical device and specifically a sensor, control unit, or both that controls a penetration depth of the surgical device or prevents movement of the surgical device into a feature of interest based upon a measurement of the feature of interest.

BACKGROUND

During some surgical procedures a site of interest is located proximate to or directly abuts a sensitive area. For example, a bowel structure may be located proximate to a wall of interest. The sensitive area (e.g., bowel) may be blindly hidden behind the feature of interest, and if the device penetrates through the wall of interest the surgical device may contact a sensitive area. Contacting the sensitive area could create trauma to the sensitive area or spread the contents in the sensitive area within the surgical site. Examples of surgical devices and puncturing tools may be found in International Patent Application Publication Nos. WO2014/066042 and WO2015/138708; European Patent Application No. EP3162294; and the devices discussed in the following websites: https://en.wikipedia.org/wiki/Veress_needle; https://en.wikipedia.org/wiki/Epidural_needle; https://en.wikipedia.org/wiki/Epidural_administration and all of which are incorporated by reference herein in their entirety for all purposes. Thus, attempts have been made to protect the sensitive areas and in many cases a more invasive surgical procedure may be used to avoid possible trauma to a sensitive area.

It would be attractive to have a surgical device with a sensor that senses a thickness of a feature of interest and then prevents the surgical device from penetrating further than a measured thickness of the feature of interest or prevents the device for activating. What is needed is a surgical device that prevents a needle of the surgical device from being deployed if the needle is set to deploy a distance that is greater than a thickness of a feature of interest. It would be attractive to have a sensor that determined a distance between a tip of a needle and an organ and prevents the tip from reaching the tip of the needle. What is needed is one or more sensors, control units, or both that control a depth of a surgical device or prevents the surgical device from being used. It would be attractive to have a sensor and signal source that communicate a distance between a first lumen and a second lumen. What is needed is a device and method to prevent perforation of a blind lumen or a feature behind a blind lumen.

SUMMARY

The disclosure meets one or more of the needs by providing. A surgical needle comprising: (a) a sensor; (b) a distal tip with the sensor being located at the distal tip; (c) a needle advancing mechanism that is adjustable to change an insertion depth; and (d) a control unit in communication with the needle advancing mechanism; wherein the sensor provides a signal to the control unit regarding a thickness of a feature of interest and the control unit controls the insertion depth based upon the signal from the sensor so that the insertion depth into the feature of interest is varied or the control unit prevents the needle advancing mechanism from activating.

The present teachings provide a surgical system comprising: (a) a surgical needle comprising: (i) a distal tip and (ii) a needle advancing mechanism that adjustably controls an insertion depth; (b) a tissue marker; (c) a sensor located on the tissue marker or the distal tip of the surgical needle; and (d) a signal source that is located on the tissue marker when the sensor is located on the distal tip of the surgical needle and is located on the distal tip of the surgical needle when the sensor is located on the tissue marker; wherein the needle advancing mechanism controls the insertion depth based upon the relationship between the tissue marker and the distal tip of the surgical needle so that the insertion depth is less than a distance between the tissue marker and the distal tip of the surgical needle or the needle advancing mechanism is prevented from advancing.

The present teachings provide: a method comprising: (a) inserting all or a portion of a surgical needle into a lumen; (b) activating a needle advancing mechanism; (c) monitoring a thickness of the lumen with a sensor; (d) receiving feedback based upon monitoring with the sensor; and (e) controlling an insertion depth of the needle advancing mechanism or preventing movement of the needle advancing mechanism based upon the feedback from the sensor.

The present teachings provide a surgical device with a sensor that senses a thickness of a feature of interest and then prevents the surgical device from penetrating further than a measured thickness of the feature of interest or prevents the device for activating. The present teachings provide a surgical device that prevents a needle of the surgical device from being deployed if the needle is set to deploy a distance that is greater than a thickness of a feature of interest. The present teachings provide a sensor that determined a distance between a tip of a needle and an organ and prevents the tip from reaching the tip of the needle. The present teachings provide one or more sensors, control units, or both that control a depth of surgical device or prevents the surgical device from being used. The present teachings provide a sensor and signal source that communicate a distance between a first lumen and a second lumen. The present teachings prevent perforation of a blind lumen or a feature behind a blind lumen.

DETAILED DESCRIPTION

Figure 1:
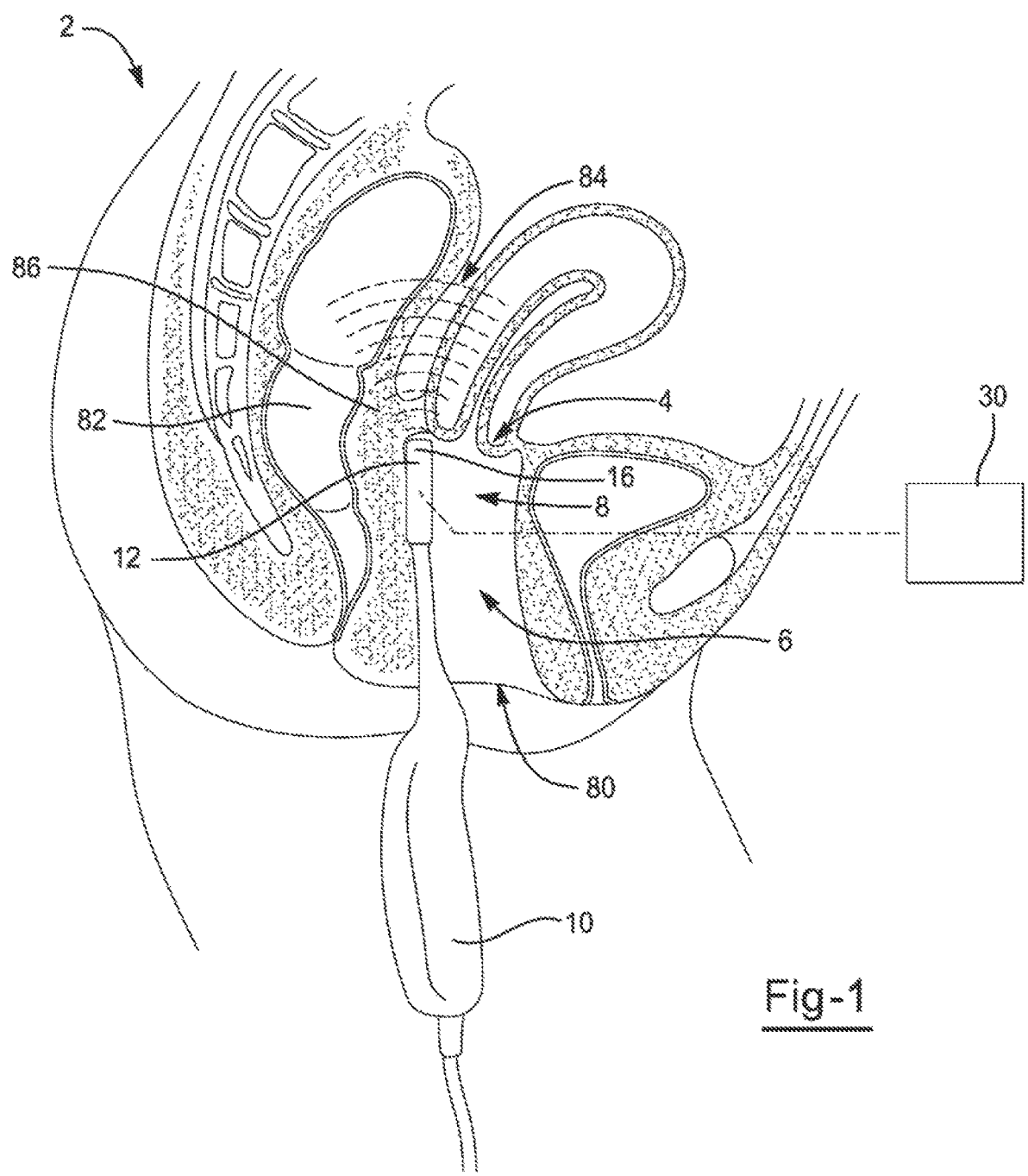
FIG. 1 is a plan view of a surgical system located within a patient.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to surgical system. The surgical system functions to operate on a lumen, a region proximate to a lumen, a blind lumen, or a combination thereof. The surgical system may include one or more cannulas, one or more needles, or both. The surgical system may puncture or penetrate tissue so that a region behind the tissue may be exposed. The surgical system may biopsy tissue or a feature of interest. The surgical system may include a surgical device, an anti-perforation device, or both.

The present teachings relate to a surgical device. The surgical device may be a non-electrical device (i.e., may only provide mechanical functions such as mechanical cutting or gripping). The surgical device may be an electrosurgical device. The surgical device may cut, puncture, open, or a combination thereof. The surgical device may be inserted into a lumen. Preferably, the surgical device may be inserted into a natural lumen. The surgical device may be inserted into a vagina, vaginal cavity, rectum, or a combination thereof. The surgical device may be an endoscope. The surgical device may be inserted through an endoscope or be an active part of an endoscope. The surgical device may be or include a cannulation device, a surgical needle, a needle, a marker, or a combination thereof. The surgical device may extend out of an endoscope and then be retracted back into the endoscope. The surgical device may puncture tissue to take a sample or create an opening. The surgical device may include be or include one or more anti-perforation devices, one or more cannulation devices, or both.

The cannulation device may function to assist in deploying a cannula, a needle, a puncturing device, or a combination thereof. The cannulation device may extend into a lumen to take a biopsy, puncture tissue, or both. The cannulation device may include one or more cannulas, surgical needles, needle advancing mechanism, needle actuators, or a combination thereof. The cannulation device may house one or more cannulas, needles, or both and assist in inserting the cannula, needle, or both into tissue, into a feature of interest, or both. The cannulation device may advance a needle, advance a cannula, or both. The cannulation device may partially enter a lumen. The full cannulation device may enter a lumen. The cannulation device may include one or more anti-perforation devices, one or more stops, one or more sensors, one or more signal sensors, or a combination thereof. The cannulation device may function to insert a needle, surgical needle, cannula, needle, or a combination thereof into tissue, a feature of interest, or both. The cannulation device may insert a cannula into tissue, through tissue, through a feature of interest, into an anatomical feature, through an anatomical feature, or a combination thereof.

The one or more cannulas may function to create an open space or maintain an open space. The one or more cannulas may create a pathway through tissue, an anatomical feature, or both that one or more surgical devices may extend through. The one or more cannulas may hold open an opening in tissue, an anatomical feature, or both. The one or more cannulas may remove tissue, puncture tissue, or both. The one or more cannulas may be removable from the tissue or anatomical feature. The one or more cannulas may temporarily be located within tissue or an anatomical feature. The cannula may have a blunt tip. The cannula may not pierce tissue, an anatomical feature, or both. A needle may be used in place of a cannula or in addition to a cannula. A needle may be located within and a cannula and extend out of a cannula.

The needle may be located within a surgical needle, a cannula, or both. The needle may function to pierce tissue, an anatomical feature, or both. The needle may have a sharp tip. The needle may have an angled tip. The needle may penetrate tissue, an anatomical feature, or both. The needle may be reciprocated one or more times. The needle may penetrate tissue, an anatomical feature, or both a plurality of times so that a biopsy or samples may be taken. The needle may create an opening that a cannula may be inserted through. The needle may puncture or penetrate tissue, an anatomical feature or both and the cannula may follow into the opening created by the needle so that the cannula may be retained when the needle is removed. The needle, cannula, or both may be part of a surgical needle.

The surgical needle may be a device that assists in inserting or placing the needle, cannula, or both into tissue, an anatomical feature, or both. The surgical needle may have a portion that extends into a lumen and a portion that is located outside of a lumen so that a user may control the surgical needle. The surgical needle may pierce tissue with a needle to create a hole, to insert a cannula, or both. The surgical needle may be a type of a cannulation device. The surgical needle may include or deploy a Veress needle, a trocar needle, or both. The surgical needle may include one or more needle advancing mechanism, one or more needle actuators, or both. The surgical needle may house all or a portion of the cannula, needle, or both. The surgical needle may have a portion that extends into a lumen. The surgical needle may have a portion that extends into a lumen to deploy a needle, cannula, or both. The surgical needle may have a portion that is hand held. The surgical needle may include a needle advancing mechanism, needle, cannula, or a combination thereof. The surgical needle has a distal tip.

The distal tip of the surgical needle may be a portion of the surgical needle that is located farthest into a lumen, that is deployed through tissue, deployed through an anatomical feature, or a combination thereof. Preferably, the distal tip of the surgical needle houses a needle, a cannula, or both. The distal tip may be moved proximate to or into contact with tissue so that the needle, cannula, or both may be moved through the tissue. The distal tip of the surgical needle may include an opening that the needle, cannula, surgical instruments, or a combination thereof pass through. The sensor, signal source, or both may be located on or at the distal end of the surgical needle. The surgical need may be a device that deploys surgical devices, needles, cannulas, or a combination thereof for performing a surgical procedure. The cannula, needle, or both may have a distal tip. The distal tip of the cannula and needle may be coplanar. The distal tip of the needle may extend beyond the distal tip of the cannula. The distal tip of the cannula may be extend beyond a distal tip of the cannula. The distal tip of the needle may extend beyond the distal tip of the cannula so that during insertion of the needle the needle penetrates tissue and then the cannula is slid over the needle to create an opening. The needle advancing mechanism may advance the needle, the cannula, or both so that a distal tip extends through tissue, an anatomical feature, or both but stops short of a protected region.

The needle advancing mechanism functions to extend a needle, a cannula, or both through tissue, a feature of interest, or both. The needle advancing mechanism may be located within or in communication with a surgical needle. The needle advancing mechanism may deploy needles, cannulas, or both out of a distal tip of the surgical needle. The needle advancing mechanism functions to control an insertion depth of a needle or cannula based upon a relationship between a tissue marker and a distal end of a needle or cannula. The needle advancing mechanism may insert a needle or cannula a distance that is less than a distance between the tissue marker and the distal end of the cannula or the needle. The needle advancing mechanism may be prevented from actuating is the distance is greater than a distance between the tissue marker and sensor. The needle advancing mechanism may extend a distal tip of the needle, cannula, or both into an open space. The needle advancing mechanism may extend a distal tip of the needle, cannula, or both to a location short of an adjacent structure, second lumen, a protected region, or a combination thereof. The needle advancing mechanism may extend a needle, cannula, or both through a wall of a vagina or uterus and into a pouch of Douglas but the distal end of the needle, cannula, or both will stop before contacting a rectum. The needle advancing mechanism may deploy a needle, cannula, or both upon pressing a button. The needle advancing mechanism may advance a needle a predetermined distance. A distance the needle advancing mechanism moves a needle may be adjusted, varied, changed, or a combination thereof. The needle advancing mechanism may have a distal tip that is placed into contact with tissue or a feature of interest and then a needle or cannula advanced through the tissue or feature of interest in contact with the needle advancing mechanism. The needle advancing mechanism may house all or a portion of a needle, cannula, or both. The needle advancing mechanism may include one or more needle actuators, control units, sensors, stops, or a combination thereof.

The one or more needle actuators may function to move one or more needles, one or more cannulas a distance. The one or more needle actuators may move a needle, a cannula, or both a predetermined distance. The one or more needle actuators may puncture tissue, a feature of interest, or both. The one or more needle actuators axially move the needle, the cannula, or both. The one or more needle actuators may move a needle, a cannula, or both at an angle relative to the tissue, the feature of interest, or both. The one or more needle actuators may move the needle, the cannula, or both with a sufficient amount of force to puncture the tissue, the feature of interest, or both. The one or more needle actuators may be variable. The one or more needle actuators may move the needle, the cannula, or both a distance of about 1 mm or more, about 2 mm or more, about 3 mm or more, about 4 mm or more, about 5 mm or more, about 1 cm or more, or about 1.5 cm or more. The one or more needle actuators may move the needle, the cannula, or both a distance of about 10 cm or less, about 7 cm or less, about 5 cm or less, or about 3 cm or less. The one or more needle actuators may include one or more bias members, one or more pneumatic systems, one or more hydraulic systems, or a combination thereof. The one or more bias members may be a spring, compressible member, rubber member, elastomeric member, a tensioning member, solenoid, pneumatic system, or a combination thereof. The one or more needle actuators may be preloaded prior to being inserted into a lumen. The one or more needle actuators may be adjusted while they were in a lumen. The one or more needle actuators may be set, reset, adjusted, or a combination thereof within a lumen, from a location external of the lumen, or both. The one or more needle actuators may include or be connected to one or more anti-perforation devices.

The one or more anti-perforation device function to protect a protected tissue, protected area, a protected area, or a combination thereof (hereinafter referred to as protected tissue). The one or more anti-perforation device may prevent actuation of the one or more needle actuators. The one or more anti-perforation devices may automatically control an actuation depth of a needle, cannula, or both. The one or more anti-perforation devices may prevent actuation of a needle, a cannula, or both if a monitored thickness is less than a set distance. The one or more anti-perforation devices may change a set distance based upon a monitored distance, based upon feedback from monitoring, or both. The one or more anti-perforation devices may control a distance the needle, cannula, or both move. The one or more anti-perforation devices may provide feedback, communicate with a control unit, move a stop, or a combination thereof. The one or more anti-perforation devices may lock a needle or cannula, make a sound, create a haptic signal, create a visual signal, or a combination thereof. The one or more anti-perforation devices may include one or more sensors, one or more control units, one or more tissue markers, or a combination thereof.

The one or more control units function to prevent a needle, a cannula, or both from contacting protected tissue. The one or more control units may move a stop, prevent actuation of a needle, prevent actuation of a cannula, adjust a distance a needle is moved, adjust a distance a cannula is moved, or a combination thereof. The one or more control units may communicate with one or more sensors, one or more signal sources, one or more detecting devices, or a combination thereof. The one or more control units may be in communication with the needle advancing mechanisms. The one or more control units may be in communication with the sensors, signal source, detecting device, stop, one or more needle advancing devices, or a combination thereof. The one or more control units may be in wired communication or wireless communication with the sensors, signal sources, detecting devices, tops, needle advancing devices, or a combination thereof. The one or more control units may control actuation of the needle advancing device. For example, the control unit may determine a depth or be provided a depth and the control unit may determine a distance of actuation and then actuate the needle advancing device, change the distance, or prevent actuation. The control units may monitor one or more distances. The control unit may monitor a distance between two lumens. The control unit may monitor a thickness of an open space. The control unit may be in communication with a sensor and a signal source and determine a distance therebetween. The control unit may communicate with only a sensor to determine a thickness. For example, if a sensor is inserted in a vaginal canal and a signal source is inserted into a rectum, the control unit may monitor a distance between the sensor and the signal source so that a needle does not extend into the colon, stops short of the colon, stops in an open space such a pouch of Douglas; or a combination thereof. The control unit may calculate a distance the needle, cannula, or both can extend. The control unit may set a stop once a distance is calculated.

The one or more stops may function to limit movement of a needle, cannula, or both to a predetermined distance, a calculated distance, a measured distance, or a combination thereof (e.g., a distance). The one or more stops may pre-compress a needle actuator, adjust a needle actuator, or both. The one or more stops may release a compression of a needle actuator. The one or more stops may be in contact a needle or needle actuator once a needle moves the distance. The one or more stops may move forward or backward to control a distance or depth the needle advances or penetrated into a feature of interest. The stop may be located inside of the needle advancing mechanism. The stop may be connected to or part of the needle actuator. The stop may be located external to the needle advancing mechanism but in communication with the needle or cannula. The needle advancing mechanism, needle actuator, or both may move the needle, the cannula, or both and the stop may determine the distance the needle penetrates into the feature of interest. The stop may be axially movable. The stop may be connected to the needle advancing mechanism and may be inserted into a lumen with the needle advancing mechanism. The stop may be electrically controlled. The stop may electrically move. The stop may be moved from a location external of the lumen. The stop may be moved by the control unit. The stop may be located in a same or a different lumen as a tissue marker, sensor, signal source, or a combination thereof.

The one or more tissue markers may function to mark protected tissue. The one or more tissue markers may connect to or be located near a protected tissue. The one or more tissue markers may mark a first lumen, a second lumen, or both. The one or more tissue markers may be inserted into a second lumen. The one or more tissue markers may locate a protected tissue so that the protected tissue is not contacted or damaged when the surgical device is in operation. The one or more tissue markers may be inserted into a lumen and be part of a surgical device. The one or more tissue markers may include a sensor, a signal source, or both. The one or more tissue markers may be part of a surgical device. The one or more tissue markers may be located on a distal tip of a surgical needle, cannula, or both. The one or more tissue markers, preferably, may be located in a different lumen or a different surgical device as the needle. The tissue markers may connect to tissue, be located in tissue, or both. The one or more tissue markers may indicate protected tissue so that a distance relative to the tissue markers can be determined. The tissue markers may be expandable within protected tissue or a lumen. The tissue markers may connect to tissue or a lumen. The tissue marker may be removably inserted into a lumen. Preferably, the tissue marker is connected to a surgical device or a finger of a surgeon and the tissue marker is located within a lumen. For example, the tissue marker may be inserted into a rectum by a surgical device or a surgeon's finger and then removed when the procedure is finished. The tissue markers may include one or more sensors.

The one or more sensors may function to measure a distance between a protected tissue and a surgical device. The one or more sensors may work without any other sensors. The sensors may sense a distance between two locations. The sensors may determine a distance between one tissue and a second tissue or an open space between two tissues (e.g., a tissue of interest and a protected tissue). The sensor may be a soft tissue thickness sensor, an ultrasonic sensor, a light reflective sensor, a conductive material thickness sensor, a capacitance sensor, or a combination thereof. The sensor may be connected to or located proximate to a distal tip of a surgical device. Preferably, the sensor is located at or on a distal tip of a needle, a cannula, or both. The sensor may determine a depth that a needle or cannula can safely advance. The sensor may determine a distance or length of an open space. The sensor may determine a distance a protected tissue is away from a distal tip. The sensor may directly or indirectly connected to a surgical device. Preferably, the sensor is directly connected to a distal tip of the surgical device. The sensor may work without a signal source. The sensor may work in conjunction with a signal source. The sensor and the signal source may be mechanically separate, electrically separate, or both.

The signal source may function mark protected tissue. The signal source may communicate with the sensor. The signal source may transmit a signal to a sensor that a sensor monitors to determine a distance. The signal source may be located within a different lumen than the sensor. The signal source may transmit a signal through tissue, an open space, an organ, or a combination thereof that is picked up by a sensor. The signal source and sensor may determine a distance between a distal tip and protected tissue. The signal source may be ultrasound, acoustic, doppler ultrasound, vibrations, or a combination thereof. The signal source and sensor may be the only two devices needed to determine a distance between two locations. If the signal source is located on the tissue marker than the sensor is located on the cannula, the needle, or both. If the signal source is located on the needle, the cannula, or both then the sensor is located on the tissue marker. A detecting device may monitor a distance between the sensor and signal source.

The detecting device may function to detect a signal between the sensor and the signal source, to calculate a distance based upon the signal transmitted from the signal source and received by the sensor, or both. The detecting device may be part of a control unit, sensor, or both. The detecting device may be part of the sensor. The detecting device may calculate a distance. The detecting device may control the stop, an insertion depth, or both. All or a portion of the detecting device may extend into the lumen or be located outside of the lumen.

The lumen may be any opening that a surgical device may extend into. Preferably, the lumen is a natural lumen. The lumen may be a vaginal canal, a rectum, urethra, mouth, ear, nose, eye socket, or the like. The lumen may be located proximate to a second lumen, an open space, or both.

The second lumen may be any of the lumen discussed herein. The lumen, second lumen, or both may receive the sensor, the signal source, a portion of a surgical device, a distal tip of a needle, a distal tip of a cannula, a needle advancing mechanism, an anti-perforation device, or a combination thereof. Preferably, if only one lumen is being operated on, only a sensor is applied. More preferably, if two lumen are being operated on or a location between two lumen is being operated on a sensor is placed in one lumen and a signal source is placed in a second lumen. A first lumen may be a vaginal canal and may receive a portion of a surgical device and a sensor and a second lumen may be the rectum and may receive all or a portion of a tissue marker, signal source, or both. An open space proximate to or located between the first lumen, the second lumen, or both may be monitored.

The open space may be any space where a needle or lumen may be inserted that may not damage or contaminate a lumen. The open space may receive the needle or cannula when the needle advancing mechanism advances the needle or cannula. The open space may provide access to a feature of interest located proximate to the lumen. The open space may be a pouch of Douglas. The open space may be located within an abdomen, sinus cavity, peritoneal cavity, or a combination thereof. The open space may be filled with a fluid, air, open, or a combination thereof. The open space may have a distance. The open space may be accessed during surgery and may be monitored by a method taught herein.

The present device and system taught herein may be used in a method to protect one or more features of interest. The device and system may include one or more anti-perforation devices. The method may include a step of protecting protected tissue. A surgical device, sensor, surgical needle, anti-perforation device, needle advancing mechanism, or a combination thereof may be inserted into a first lumen, a second lumen, or both. A sensor may be inserted into a first lumen (e.g., a vaginal canal). A signal source may be inserted into a second lumen (e.g., a rectum). The sensor may measure a thickness or a lumen, a distance between a distal tip and a protected tissue, an open space, or a combination thereof. The sensor may measure without any other devices. The sensor may communicate with a signal source. The sensor may receive a signal. The signal source may transmit one or more signals to the sensor. The sensor, a detecting device, or both may determine a distance. A needle depth may be adjusted based upon feedback from the detecting device, control unit, or both. The needle plunge or insertion depth may be varied by moving a stop. The insertion depth or plunge depth may be varied by adjusting one or more parameters of the needle advancing mechanism, the needle actuator, or both. The tissue marker may be placed. The surgical device may be inserted. The needle actuator may be activated. The needle, cannula, or both may be inserted a depth. The needle, cannula, or both may be prevented from actuating, advancing, being inserted, or both. Feedback from the sensor, detecting device, control unit, or a combination thereof may be monitored. A distance may be calculated. The distance may be provided as feedback. The sensor, signal source, or both may be removed from the lumen, the second lumen, or both. Adjusting an insertion depth of a needle, cannula, or both. Providing feedback between the control unit and the needle advancing mechanism, the stop, the needle actuator, or both.

FIG. 1 is plan view of a surgical system 2 within a lumen 80 of a patient. The surgical system 2 includes an anti-perforation device 6 and a surgical needle 10 having a distal tip 16. The surgical needle 10 as shown is also a surgical device 4 and cannulation device 8. The distal tip 16 of the surgical needle 10 includes a sensor 12 that measures a thickness of tissue 86 (e.g., as shown is the peritoneal wall). The sensor 12 measures the thickness of the tissue so that when a needle is deployed, the needle does not contact a second lumen 82, which as shown is a colon. The lumen 80 and the second lumen 82 are separated by an open space 84. The sensor 12 is connected to a control unit 30 that assists in measuring the thickness of the tissue, the distance between the lumen 80 and the second lumen 82, controlling the surgical needle, or a combination thereof.

Figures 2A, 2B:
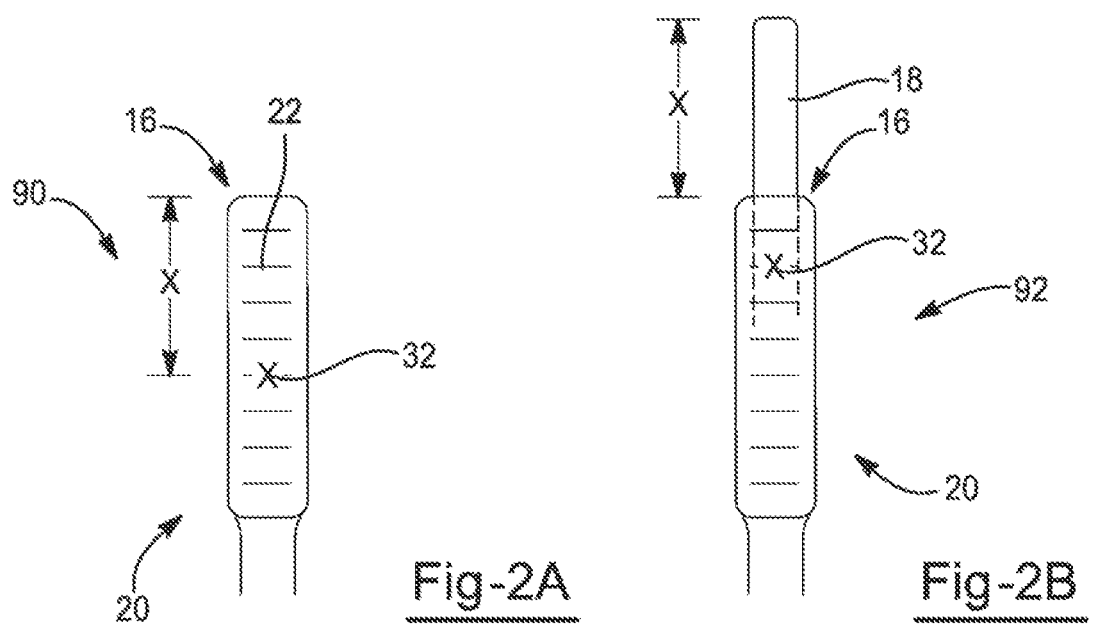
FIG. 2A is a needle advancing mechanism with the needle in a retracted position and a stop position set.
FIG. 2B is a needle advancing mechanism with the needle in a deployed position.

FIG. 2A illustrates a distal tip 16 of a surgical device having a needle advancing mechanism 20 with a needle actuator 22. The needle advancing mechanism 20, as shown, is in the retracted position 90. The needle advancing mechanism 20 includes a stop 32 that limits movement of the needle (no shown) when the needle actuator 22 is activated. The stop 32 sets an actuation distance (X) of the needle.

FIG. 2B illustrates the needle 18, in the deployed position 92, extending from the distal tip 16 of the needle advancing mechanism 20. The needle 18 extends the distance (X) because the stop 32 restricts movement of the needle 18.

Figure 3:
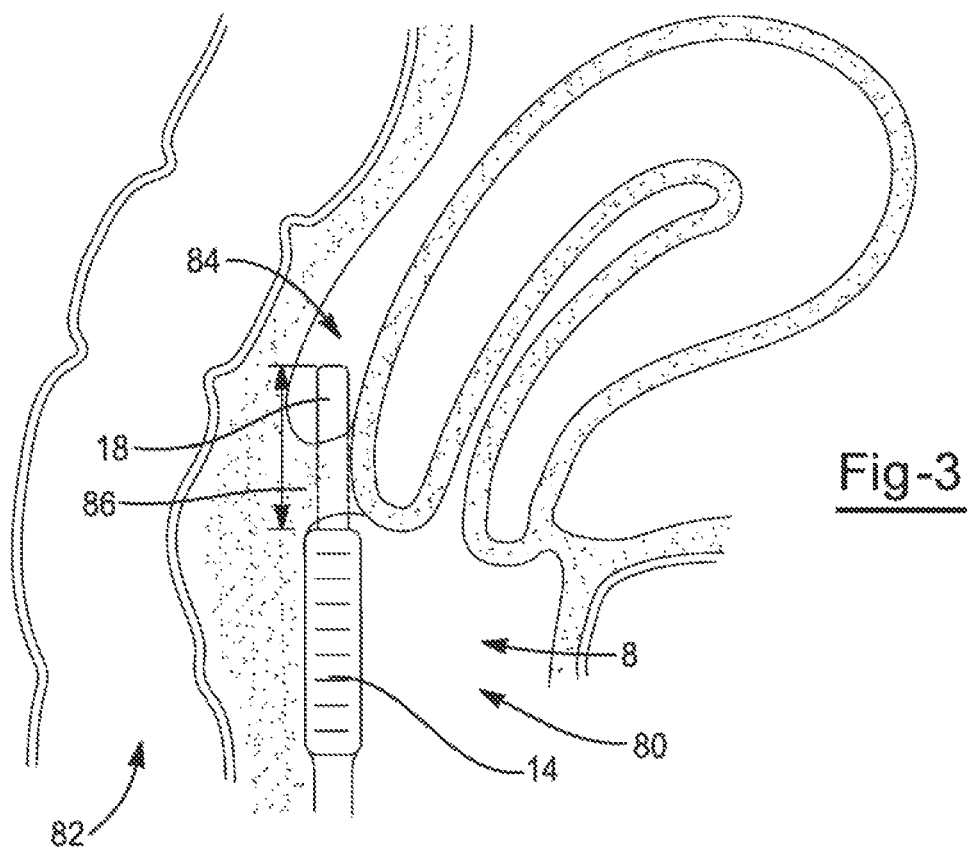
FIG. 3 is a plan view of a surgical system with the needle advanced into an open space.

FIG. 3 illustrates a cannulation device 8 with a needle 18 extending from the lumen 80 through the tissue 86 and into the open space 84, without contacting the second lumen 82.

Figure 4:
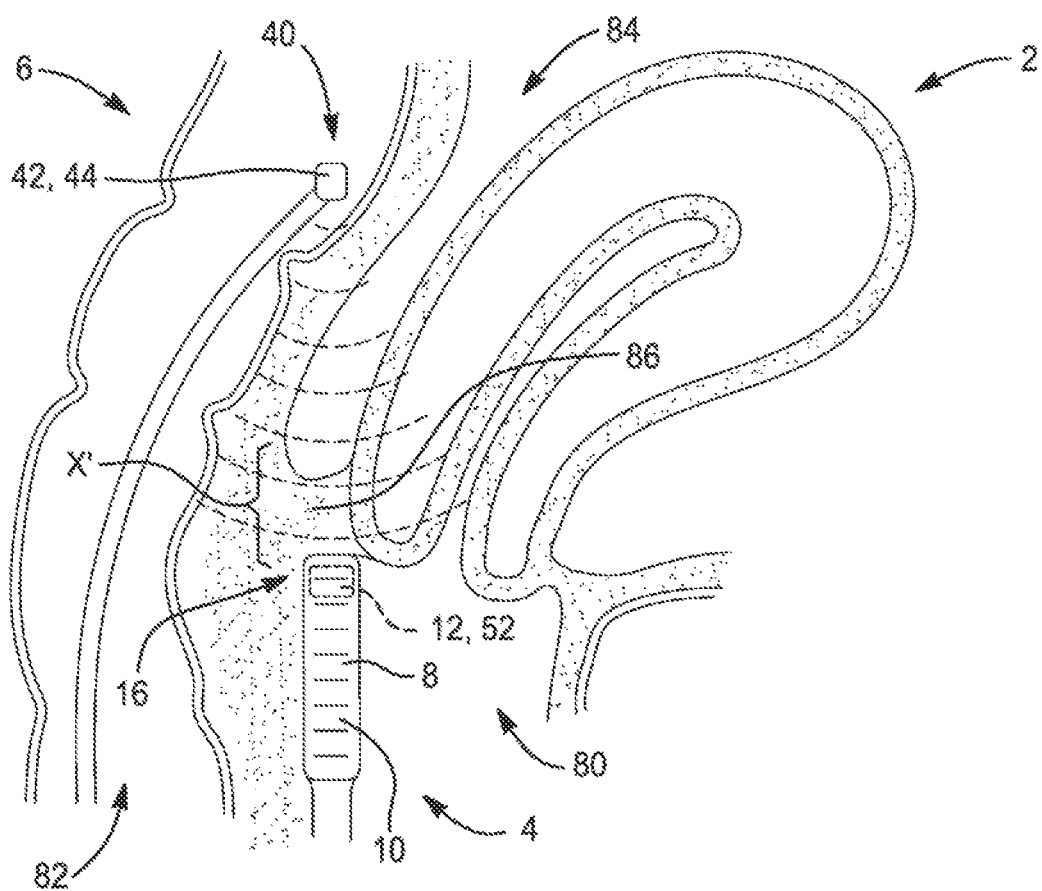
FIG. 4 is a plan view of a surgical system with a sensor located in a first lumen and a signal source 44 in a second lumen.

FIG. 4 illustrates a surgical system 2 with a surgical device 4 and an anti-perforation device 6. The surgical device 6 is both a surgical needle 10 having a cannulation device 8, a sensor 12, or a detecting device 52 (the detecting device may also be located outside of the lumen and/or surgical device). The anti-perforation device 6 also includes a tissue marker 40, which as shown includes a signal source 44 (but may include a sensor 42). The surgical needle 10 extends into a lumen 80 and contacts a first side of tissue 86 and the tissue marker 40 is inserted into a second lumen 82. A signal is sent from the signal source 44 in the tissue marker 40 to the sensor 12 in the distal tip 16 of the surgical needle 10 to determine a distance between the lumen 80 and the second lumen 82 and if the open space 84 is sufficiently large that the needle (not shown) can be deployed without contacting the second lumen 82. If the distance is not large enough a control unit (not shown) may prevent deployment of the needle (not shown).

Figure 5A:
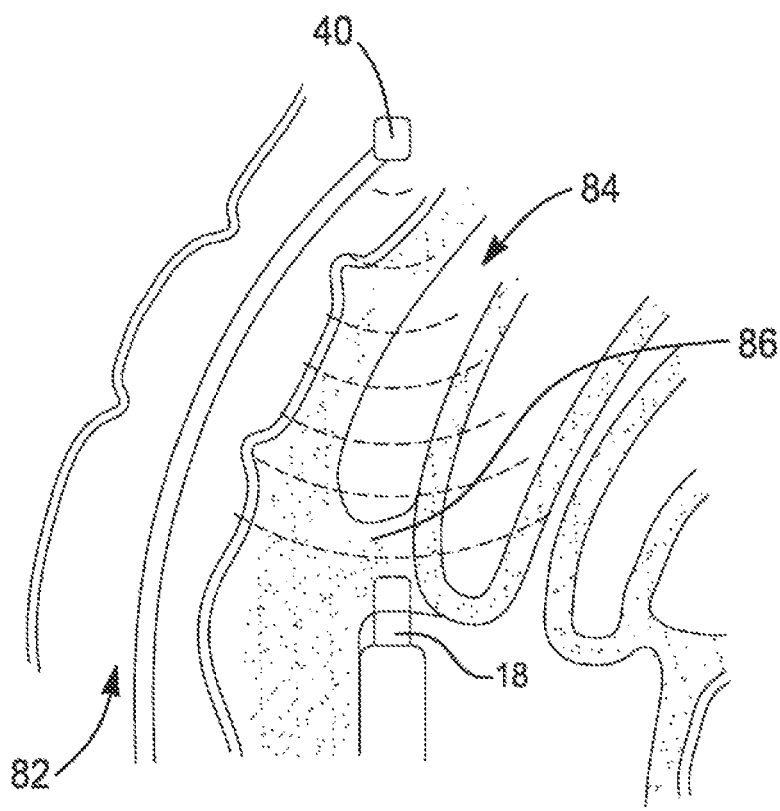
FIG. 5A illustrates the needle partially advancing into tissue.

FIG. 5A illustrates a needle 18 partially puncturing the tissue 86 and extending towards the open space 84 and the tissue marker 70.

Figure 5B:
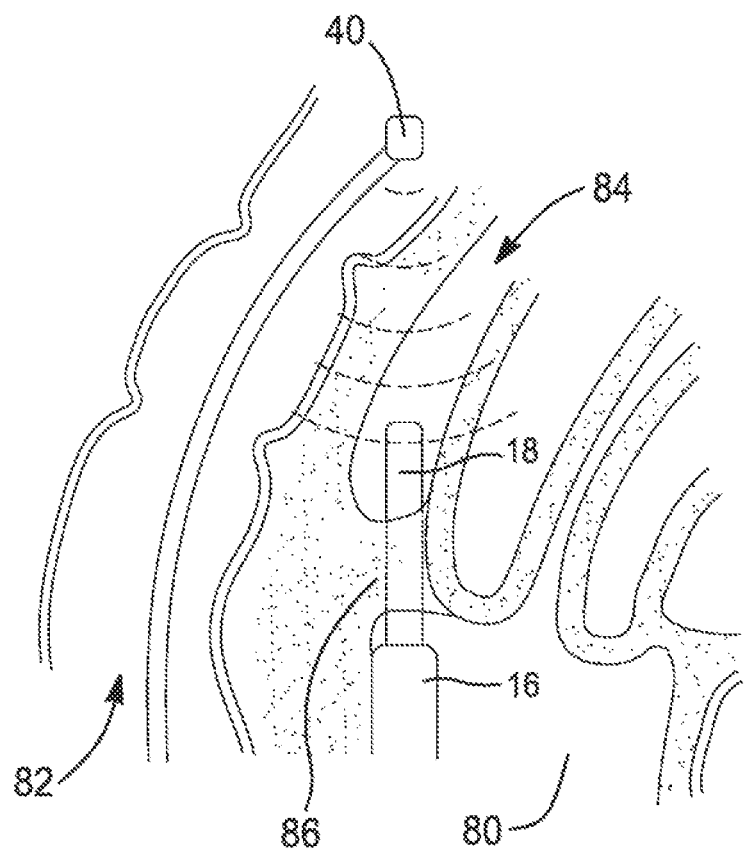
FIG. 5B illustrates the needle advanced through the tissue and into an open space.

FIG. 5B illustrates the needle 18 extending beyond the distal tip 16 to a fully deployed position and stopping in the open space 84 between the lumen 80 and the second lumen 82 due to a measured distance between the distal tip 16 and the tissue marker 40.

Figure 6:
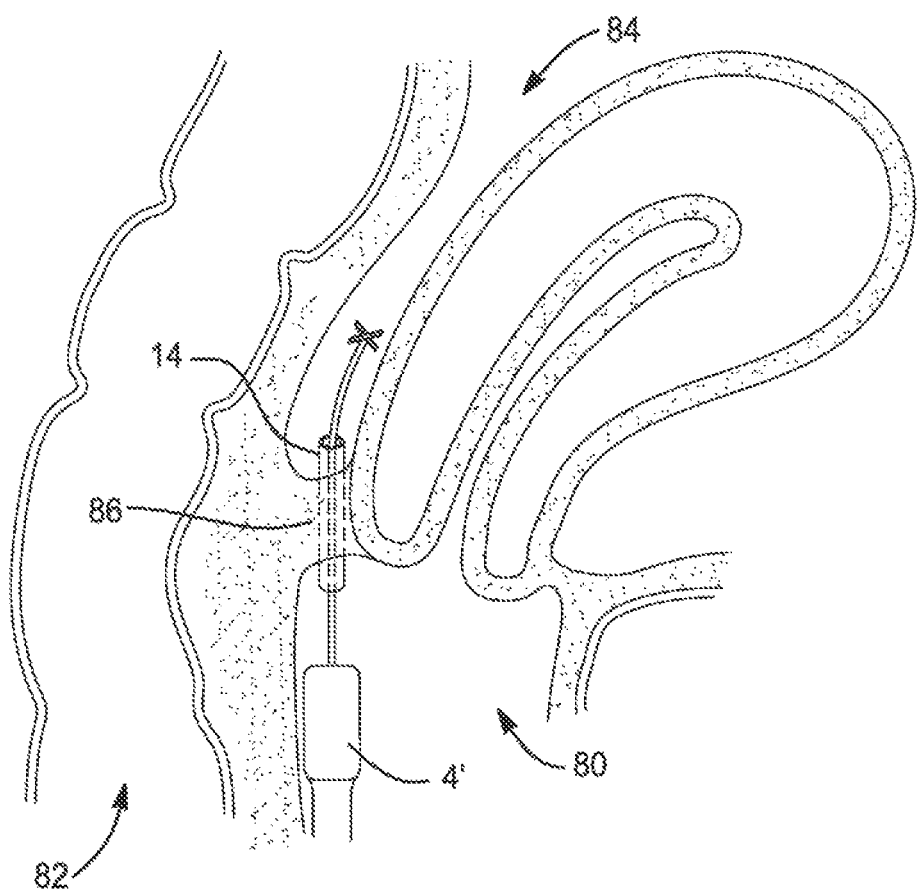
FIG. 6 illustrates a cannula advanced through tissue into an open space.

FIG. 6 illustrates a second surgical device 4' inserted into a lumen 40 after a cannula 14 has been inserted into tissue 86 creating a space through the tissue 86 from the lumen 80 into an open space 84 but short of the second lumen 82. The cannula 14 provides temporary access to the open space 84 to perform a surgical procedure.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. Unless otherwise stated, a teaching with the term "about" or "approximately"

in combination with a numerical amount encompasses a teaching of the recited amount, as well as approximations of that recited amount. By way of example, a teaching of "about 100" encompasses a teaching of within a range of 100+/−15.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Surgical system
4 Surgical device
6 Anti-perforation device
8 Cannulation device
10 Surgical needle
12 Sensor
14 Cannula
16 Distal tip (of cannula)
18 Needle
20 Needle advancing mechanism
22 Needle actuator (solenoid, spring, pneumatic system)
30 Control unit
32 stop
40 Tissue Marker
42 sensor
44 Signal source
50 Detecting device
80 Lumen (blind lumen)
82 Second Lumen
84 Open space
86 tissue
90 Retracted position
92 Deployed position

We claim:

1. A method comprising:
positioning a distal tip of a surgical device adjacent to a first tissue surface, the surgical device including a needle configured to advance from a retracted position to a deployed position by a penetration distance;
determining a measured distance between the first tissue surface and a second tissue surface with a sensor at the distal tip of the surgical device, wherein the first tissue surface is located within a first lumen of a patient and the second tissue surface is located within a second lumen of the patient;
comparing the penetration distance to the measured distance; and
controlling the surgical device such that:
when the penetration distance is less than the measured distance, advancement of the needle to the deployed position is allowed; and
when the penetration distance is greater than the measured distance, advancement of the needle to the deployed position is prevented.

2. The method of claim 1, wherein the surgical device further includes a needle advancing mechanism operable to advance the needle from the retracted position to the deployed position.

3. The method of claim 2, wherein the needle advancing mechanism includes an adjustable stop that is controllable to change the penetration distance of the needle.

4. The method of claim 3, wherein the adjustable stop is disposed internally within the surgical device.

5. The method of claim 3, further comprising:
controlling the adjustable stop to change the penetration distance of the needle.

6. The method of claim 1, further comprising:
positioning a tissue marker adjacent to the second tissue surface, the tissue marker including a signal source.

7. The method of claim 6, wherein the signal source is located at a distal tip of the tissue marker.

8. The method of claim 6, wherein determining the measured distance between the first tissue surface and the second tissue surface comprises sending a signal from the signal source of the tissue marker to the sensor of the surgical device.

9. A method comprising:
positioning a distal tip of a surgical device adjacent to a first tissue surface within a first body lumen of a patient, the surgical device including a needle configured to advance from a retracted position to a deployed position by a penetration distance;
positioning a distal tip of a tissue marker adjacent to a second tissue surface within a second body lumen of the patient;
determining a measured distance between a sensor at the distal tip of one of the surgical device or the tissue marker and a signal source at the distal tip of the other one of the surgical device or the tissue marker;
comparing the penetration distance to the measured distance; and
preventing advancement of the needle to the deployed position when the penetration distance is greater than the measured distance.

10. The method of claim 9, wherein the surgical device further includes a needle advancing mechanism operable to advance the needle from the retracted position to the deployed position and an adjustable stop operable to change the penetration distance of the needle.

11. The method of claim 10, further comprising:
controlling the adjustable stop to change the penetration distance of the needle.

12. The method of claim 11, wherein the adjustable stop is disposed internally within the surgical device.

13. A method comprising:
positioning a surgical device within a vaginal canal of a patient at a location adjacent to a target tissue, the surgical device including a needle and a needle advancing mechanism, the needle advancing mechanism including an adjustable stop that is controllable to limit movement of the needle;
monitoring a thickness of the target tissue with a sensor located on the surgical device within the vaginal canal of the patient;
receiving feedback based upon monitoring with the sensor; and
controlling an insertion depth of the needle advancing mechanism or preventing movement of the needle advancing mechanism based upon the feedback from the sensor.

14. The method of claim 13, wherein the adjustable stop is disposed internally within the surgical needle.

15. The method of claim 13, wherein the sensor is a soft tissue thickness sensor.

16. The method of claim 13, wherein the sensor is an ultrasonic sensor, a light reflective sensor, a conductive material thickness measurement sensor, a capacitance sensor, or a combination thereof.

17. The method of claim 13, wherein controlling the insertion depth of the needle advancing mechanism comprises controlling a location of the stop to determine the depth the needle penetrates into the target tissue.

18. The method of claim 13, wherein monitoring the thickness of the target tissue comprises positioning a signal source within a rectum of the patient and monitoring a signal created by the signal source with the sensor positioned within the vaginal canal of the patient.

* * * * *